United States Patent [19]

MacKenzie et al.

[11] Patent Number: 4,981,684

[45] Date of Patent: Jan. 1, 1991

[54] FORMATION OF ADJUVANT COMPLEXES

[75] Inventors: Neill M. MacKenzie, St. Albans; Angela M. O'Sullivan, Berkhamsted, both of Great Britain

[73] Assignee: Coopers Animal Health Limited, United Kingdom

[21] Appl. No.: 426,050

[22] Filed: Oct. 24, 1989

[51] Int. Cl.$^5$ ............................................. A61K 39/00
[52] U.S. Cl. ...................... 424/88; 530/403; 530/405; 530/406
[58] Field of Search ............... 424/88, 89; 530/403, 530/405, 406

[56] References Cited

U.S. PATENT DOCUMENTS 4,578,269  3/1986  Morein ................................. 424/88

FOREIGN PATENT DOCUMENTS 0142192  5/1985  European Pat. Off. ............. 424/88
0231039  8/1987  European Pat. Off. ............. 424/88

OTHER PUBLICATIONS

Morein, B. et al., (1984), *Nature* 308, 457–460.

*Primary Examiner*—Margaret Moskowitz
*Assistant Examiner*—R. Keith Baker

[57] ABSTRACT

"Iscom" adjuvant matrices, comprising a sterol, a glycoside, a solubilized water-insoluble antigen and, optionally, a phospholipid, may be formed without removing the solubilizing agent used for the antigen. The glycoside is preferably Quil A and the sterol is preferably cholesterol.

6 Claims, No Drawings

FORMATION OF ADJUVANT COMPLEXES

The present invention relates to processes for the formation of complexes having adjuvant activity, the complexes comprising lipid and at least one glycoside.

Prophylactic immunisation of animals against microbes comprises administration of an antigen derived from the microbe in conjunction with a material that increases the antibody and/or cell-mediated immune response of the antigen in the animal. This material is known as an adjuvant. The only adjuvants currently authorised for use in humans or pigs in many countries are aluminium hydroxide and aluminium phosphate. Although these adjuvants are sufficient for many vaccines, studies have shown that Freund's complete adjuvant (FCA) or Quil A (also known as saponin) are often more efficacious in eliciting antibody response and cell mediated immunity but unfortunately these adjuvants may cause the animals to react adversely to vaccination.

No. EP-A-0 109 942 and No. EP-A-0 180 564 describe immunogenic complexes formed between glycosides, such as triterpenoid saponins (particularly Quil A), and antigens which contain a hydrophobic region. These immuno-stimulating complexes have been given the name "iscoms". The amount of Quil A in an iscom can be about 10 to 100 times lower than when Quil A is mixed with the antigen to produce the same antigenic effect. Iscoms do not create the adverse reactions associated with Quil A.

No. EP-A-231 039 indicates that the presence of antigen is not necessary for formation of the basic iscom structure, hereafter referred to as the iscom "matrix", it being possible to form the matrix from a sterol, such as cholesterol, a phospholipid, such as phosphatidylethanolamine, and a glycoside such as Quil A.

In all three of the cited prior art documents, when a water-insoluble antigen was used, this was solubilised with a detergent and then, after mixing with the glycoside etc, the detergent was removed, for example by dialysis, to cause formation of the iscoms. We have now found that iscoms will form in the presence of detergent and that this removal step is unnecessary.

One aspect of the invention provides a process for making an immunogenic complex comprising a water-insoluble antigen, the process comprising solubilising the antigen with a solubilising agent, admixing the solubilised antigen, a glycoside, a sterol and, optionally, a phospholipid and forming an iscom substantially without removal of the solubilising agent.

The invention also encompasses a vaccine prepared by such a process for human or animal use.

By "animal", we mean non-human vertebrate, preferably a mammal such as a cow, pig, sheep, goat, horse, dog or cat.

The vaccine may comprise one or more diluents and carriers of a conventional nature.

By "antigen" we mean any entity capable of producing a protective antibody or cell-mediated immunological response against a pathogenic organism in a vertebrate exposed to the antigen. The antigen may be all or part of a protein, glycoprotein, glycolipid, polysaccharide or lipopolysaccharide which is associated with the organism, or it may be a polypeptide or other entity which mimics all or part of such a protein, glycoprotein, glycolipid, polysaccharide or lipopolysaccharide. Because the antigen may or may not be incorporated in the iscom matrix during formation of the latter, If it is not incorporated, it is not necessary for it to have a hydrophobic region or to be linked to a hydrophobic group, as in prior art procedures. The organism itself need not be present in the vaccine but it can reduce the cost of the vaccine if whole cells, for example of *Haemophilus pleuropneumoniae*, are used instead of extracts. Pathogenic organisms include viruses, bacteria, mycoplasmas, fungi, protozoa and other parasites. By "mycoplasma", we include the closely related organisms known as ureaplasmas and acholeplasmas.

Bacteria of medical or veterinary interest include Mycobacterium (e.g. *M. tuberculosis*), Clostridium (e.g. *C. welchii*), Rickettsia, Spirochaetes (e.g. *T. pallidum*), Escherichia (e.g. *E. coli*), Staphylococci (e.g. *S. aureus*), Haemophilus (e.g. *H. influenzae* and *H. Pleuropneumoniae*, Bordetella, (e.g. *B. pertussis*), Vibrio (e.g. *V. cholerae*), Salmonella (e.g. *S. typhi* and *S. paratyphi*) Streptococci (e.g. *S. aqalatiae*), Neisseria (e.g. *N. gonorrhoea*), Pasteurella (e.g. *P. multocida*), Legionella (e.g. *L. pneumoniae*), Pseudomonas (e.g. *P. malliae*), Actinobacillus (e.g. *A. pleuropneumoniae*), Campylobacter (e.g. *C. jejuni*) and Listeria (e.g. *L. monocytogenes*). Particular antigens include the adherence factor in Coli, e.g. pili K 88, porin protein in e.g. Salmonella and outer membrane proteins from *B. pertussis* and *Neisseria meningitidis*.

Vaccination of pigs against *H. pleuropneumoniae* is particularly preferred.

Mycoplasmas of veterinary or medical interest include *Mycoplasma bovis*, *M. gallisepticum*, *M. agalactiae*, *M. hyopneumoniae*, *M. pneumoniae*, *M. synoviae*, *M. arthritidis*, *M. capricolium*, *M. dispar*, *M. hominis*, *M. mycodiessubs capri*, *M. orale*, *M. oripneumoniae*, *M. pulmonis*, *M. cynos*, *M. hyorhinis*, *M. mycoides*, *M. salvarium* and *M. fermentans*.

Fungi associated with disease include: Candida spp., Cryptococcus spp., Aspergillus spp., Microsporum spp., Trichophyton spp. Epidermophyton spp. and Dermatophilus spp.

Parasites associated with disease include: Toxoplasma spp. such as *T. gondii*, Plasmodium spp. such as *Plasmodium vivax*, *P. malariae*, *P. falciparum* and *P. ovale*, Teileria spp. such as *T. parvum*, Eimeria spp. such as *E. tenella*, *Entamoeba histolytica*, anaplasma of various types, trematodes such as *Schistosoma Haematobium*, *S. mansoni*, and *S. japonicum*, trypanosomes, such as *Trypanosoma gambiense*, *T. brusei*, *T. congolesi* and *hepatica fasciola*, nematodes, such as Ascaris, Wuchereria, *Toxocara canis* and Onchocerca spp., and cestodes, such as Taenia spp., especially *T. ovis*.

Viruses associated with disease include: Orthomyxoviridae such as influenza A,B,C, Paramyxoviridae, especially measles virus, mumps virus, parainfluenza 1,2,3, and 4 viruses, canine distemper virus and rinderpest virus, Rhabdoviridae, especially rabies virus, Retroviridae, especially feline leukaemia virus and bovine leukaemia virus, Herpesviridae, especially Pseudorabies, Coronaviridae (esp. bovine), Togaviridae, such as EEE, WEE, VEE (eastern, western and Venezuela equine encephalitis), yellow fever virus, bovine virus diarrhoea virus, equine herpes virus and European swine fever virus, Parvoviridae (esp. FMDV), Adenoviridae (esp. canine), Papovaviridae, Reoviridae (e.g. rotavirus), Caliciviridae, Rhinoviridae, Aphthoviridae, Flaviviridae, Pestiviridae, Morbilliviridae, Orbiviridae, Arenaviridae, Poxviridae, Bunyaviridae, Iridioviridae, especially African swine fever virus and, among unclassified viruses, human hepatitis β-virus and Marburg/Ebola virus. Many of these have envelopes from which suitable antigens can be extracted.

If the antigen is not incorporated in the iscom matrix as part of the iscom structure itself, it may be present on the outside of the iscom matrix or it may subsequently be integrated into the iscom matrix. Alternatively, it may be present entirely separately in solution or dispersion. Such processes and compositions are disclosed in U.S. Ser. No. 07/426,589, filed concurrently herewith and entitled "Adjuvant Complexes", the entire contents of which are incorporated herein by reference.

The iscom matrix may be prepared in the way disclosed in No. EP-A-0 231 039, namely by mixing together solubilised sterol, glycoside and (optionally) phospholipid but with the removal of the solubilising agent being omitted. An electron micrograph of iscoms obtained from Quil A, cholesterol and phosphatidylethanolamine is depicted in FIG. 1 of No. EP-A-0 231 039 (magnification 116.000 x). If phospholipids are not used, two dimensional structures are formed. An example of such structures is depicted in FIG. 2 of No. EP-A-0 231 039. This figure is an electron micrograph (magnification 146.000 x) of structures obtained from Quil A and cholesterol. The term "iscom matrix" is used to refer to both the 3-dimensional and 2-dimensional structures.

The glycosides to be used in the process according to the invention may be the same as those mentioned in No. EP-A 0 109 942 and No. EP-A-0 231 039, the entire contents of which are incorporated herein by reference. Generally the glycosides are glycosides showing amphipathic properties and comprise hydrophobic and hydrophilic regions in the molecule. Preferably saponins are used, especially the saponin extract from *Quillaja saponaria* Molina in the first place DQ-extract prepared according to K. Dalsgard: Saponin Adjuvants. Bull. Off. Int.. Epiz. 77 and 7-8) 1289–1295 (1972) and Quil A, also prepared according to K. Dalsgaard: Saponin Adjuvants III Archiv für die gesamte Virusforschung 44, 243–254 (1974). Other preferred saponins are aescine from *Aesculus hippocastanum* (T Patt and W Winkler: Das therapeutisch wirksame Prinzip der Rosskaatanie (*Aesculus hippocastanum*) Arzneimittelforschung 10 (4) 273–275 (1960) and sapoalbin from *Gypsophilla struthium* (R Vochten. P. Joos and R Ruyssen: Physicochemical properties of sapoalbin and their relation to the foam stability. J. Pharm. Belg. 42 213–226 (1968)). The use of Quil A is especially preferred.

In the process according to the invention the glycosides are used in at least the critical micelle-forming concentration. In the case of Quil A this concentration is about 0.03% by wt. Generally, the molar ratio of glycoside (especially when it is Quil A) to sterol (especially when it is cholesterol) to phospholipid is 1:1:0–1, ±20% (preferably no more than ±10%) for each figure. This is equivalent to a weight ratio of about 5:1 for the Quil A: cholesterol.

The sterols used in the process according to the invention may be known sterols of animal or vegetable origin, such as cholesterol, lanosterol, lumisterol, stigmasterol and sitosterol. Preferably, cholesterol is the sterol used in the process according to the invention.

It is preferred for a phospholipid to be used, so that 3-dimensional iscoms are formed. Suitable phospholipids include phosphatidylcholine and phosphatidylethanolamine.

The solubilising agent may be any of those mentioned in No. EP-A-0 109 942 or No. EP-A-0 231 039, for example a detergent, urea or guanidine.

Generally, a non-ionic, ionic or zwitter-ionic detergent or a cholic acid based detergent, such as sodium desoxycholate, can be used for this purpose. Preferably, the detergent used is octylglucoside, nonyl N-methyl glucamide or decanoyl N-methyl glucamide but alkylphenyl polyoxyethylene ethers are also suitable, especially a polyethylene glycol p-isooctyl-phenylether having 9 to 10 oxyethylene groups which is commercialized under the trade name Triton X-100R.

Because, in the process of the invention, the solubilising agent need not be removed for formation of the iscoms, there is no need for any ultrafiltration, dialysis, ultracentrifugation or chromatographic step in order for the iscoms to be formed.

The process according to the invention may be used for the preparation of immunogenic complexes from antigenic proteins or peptides which show amphipathic properties. These proteins or peptides may be membrane proteins or membrane peptides isolated from viruses, bacteria, mycoplasmas, protozoa, helminths or other parasites or animal cells. It is known that the serine and threonine radicals present in the hydrophobic region (the membrane domain) of some viral membrane proteins may be esterified. Non-membrane proteins and non-membrane peptides without the desirable hydrophobic properties may be incorporated into the immunogenic complexes after coupling these with peptides consisting of hydrophobic amino acids, with fatty acid radicals, with alkyl radicals and the like. Viruses which do not have an envelope but which can yield antigens for coupling to hydrophobic groups include Picornaviridae such as foot-and-mouth disease virus, polio virus, Adenoviridae, Parvoviridae, such as feline pest virus and swine parvovirus, and Reoviridae, such as rotavirus. The proteins or peptides may also be prepared synthetically or by means of recombinant DNA techniques. Generally, ultracentrifugation or dialysis is not sufficient for the purification of an antigenic protein or peptide of natural origin. Preferably, the antigens are purified by means of chromatography, e.g. on a column of DEAE-Sephadex or by means of immuno affinity chromatography.

Suitable methods for isolation of antigens and linking to hydrophobic groups are described in No. EP-A-109 942.

The dissolved or solubilized antigen is generally contacted with a solution containing the glycoside in at least the critical micelle-forming concentration, a sterol, and optionally a phospholipid.

If desired, the solutions of the immunogenic complexes obtained may be lyophilized. The lyophilized preparations may then be reconstituted before use by addition of water.

Further, the invention relates to a pharmaceutical composition containing immunogenic complexes prepared by means of the first aspect of the invention. These properties may be obtained by preparing the immunogenic complexes in a form suitable for parenteral administration, preferably injectable administration and, in particular, for injection by the sub-cutaneous or intra-muscular routes. Generally, the pharmaceutical compositions contain the immunogenic complexes in an aqueous, physiologically acceptable medium, which, if desired, contains a buffer and/or a salt such as sodium chloride for adaptation of the osmotic pressure. These procedures are all well known in the art.

The following non-limiting examples illustrate various preferred aspects of the invention.

EXAMPLES 1-6:

Empty Iscom Matrix Preparation

Reagents Required

Phosphate Buffered Saline (Dulbecco A, Oxoid)
Lipid Mix (see below)
10% w/v solution of Quil A (Superfos) in sterile distilled water.

Preparation of Lipid Mix (10 ml)

Materials (1) Chloroform (analar)
(2) Cholesterol (Grade I, from porcine liver, Sigma)
(3) L$\alpha$ phosphatidyl choline (Sigma)
(4) Mega 9 or 10 (Sigma) or Triton. (Mega 9 is nonyl N-methyl glucamide, whereas Mega 10 is decanoyl N-methyl glucamide).
(5) Sterile distilled water

Method (a) Prepare 20% w/v of Mega 10 in sterile distilled water: i.e. weigh out 2 g Mega 10 and dissolve in 10 ml of water.
(b) Weigh 50 mg cholesterol and add to 50 mg of phosphatidyl choline.
(c) When the cholesterol has dissolved in the phosphatidyl choline add 2 ml of chloroform.
(d) Add the 10 ml of 20% w/v Mega 10. The mixture will be milky-white in appearance. This will raise the volume to 12 ml. However, the chloroform will evaporate upon stirring and the final 10 ml volume will be achieved.
(e) Stand on a magnetic stirrer in the hot room (37° C.), with the lid of the container removed. Upon continued stirring, the mixture will become more mobile and clear.
(f) Store at room temperature.

EXAMPLE 1

(1) Place 20 ml of PBSA into a sterile universal flask.
(2) Add 100 $\mu$l of a 10% solution of Quil A.
(3) Add 400 $\mu$l of the lipid mix.
(4) Whirlymix the solution at full speed for 10 seconds.
(5) Sterilise solution via passing through a 0.2 $\mu$m filter (Millipore).
(6) Decant small volume for Electron microscopy studies.
(7) Store at +4° C.

EXAMPLE 2

The method of Example 1 was followed, but with the following variants.
(1) Place 20 ml of PBSA into a sterile universal flask.
(2) Add 200 $\mu$l of a 10% solution of Quil A.
(3) Add 800 $\mu$l of the lipid mix.
(4) Whirlymix the solution at full speed for 10 seconds.
(5) Sterilise through a 0.2 $\mu$m filter.
(6) Decant a small volume for electron microscopy studies.
(7) Store at +4° C.

EXAMPLE 3

(1) 20 ml PBSA was added to an Amicon stirred cell with a 30K Mwt cut-off membrane.
(2) To this was added 800 $\mu$l of the lipid mix plus 200 $\mu$l of Quil A (10% solution).
(3) The solution was concentrated to 5 ml and 100 ml PBSA added.
(4) The above step was repeated x2.
(5) The 20 ml contents were filtered through a 0.2$\mu$ filter labelled and stored at +4° C.

EXAMPLE 4

(1) 20 ml PBSA was added to an Amicon stirred cell with a 30K Mwt cut-off membrane in place.
(2) 400 $\mu$l of the lipid mix plus 100 $\mu$l of a 10% Quil A solution was added.
(3) The above solution was concentrated to 5 ml and resuspended to 100 ml with PBSA.
(4) The above step was repeated x2.
(5) The final 20 ml contents of the cell were then filter sterilised through a 0.2 $\mu$m filter, labelled and stored at +4° C.

EXAMPLE 5

(1) 20 ml PBSA was added to an Amicon stirred cell, a 30K Mwt cut-off membrane being in place.
(2) 200 $\mu$l of the lipid mix plus 50 $\mu$l of a 10% Quil A solution was added.
(3) The above solution was concentrated to 5 ml and resuspended in 100 ml PBSA.
(4) The above step was repeated x2.
(5) The final 20 ml prep of the cell was then filtered through a 0.2 $\mu$m filter, labelled and stored at +4° C.

EXAMPLE 6

(1) 20 ml PBSA was added to an Amicon stirred cell (30K Mwt cut-off membrane).
(2) 100 $\mu$l of the lipid mix plus 25 $\mu$l of a 10% Quil A solution was added.
(3) The above solution was concentrated to 5 ml and resuspended with 100 ml PBSA.
(4) The above step was repeated x2.
(5) The final 20 ml contents of the cell were filter sterilised through a 0.2 $\mu$m filter, labelled and stored at +4° C.

In electron microscopy studies, these iscom matrices appeared to be less numerous than in the other examples.

EXAMPLE 7:

Mouse Studies: Efficacy

Female mice of an inbred strain (Balb/C) and of the same age (6-8 weeks) were used. The mice were obtained from the barrier maintained (SPF) unit of Harlan-Olac (Bicester). The National Cell Type Collection strain of *Mycoplasma hyopneumoniae* was used throughout this study. The organism was cultured in a modification of Friis medium. The stock cultures were maintained at $-70°$ C. Each suspension for vaccine incorporation was prepared by inoculating 40 ml of broth with 4 ml of the stock culture at pH 7.4 and then incubating at 37° C. for 3 days or until the pH dropped to 6.8. By this time the organism had reached the log phase of growth. The cultures were inactivated using binary ethylene imine, concentrated using tangential flow ultrafiltration, and washed with phosphate buffered saline (PBS). The concentration of antigen was adjusted such that all vaccines contained 10 $\mu$g total protein per 0.1 ml mouse dose of vaccine.

The iscom preparations of Examples 3 to 6 were used as follows.

Eight groups of six mice were immunised on two occasions, each mouse receiving 0.1 ml of the following preparations.

| Group | Vaccinate |
|---|---|
| A | 10 μg M. hyopneumoniae alone |
| B | 10 μg M. hyopneumoniae adjuvanted with Freund's Complete |
| C | 10 μg M. hyopneumoniae with iscom matrix containing 10 μg QA/mouse dose |
| D | 10 μg M. hyopneumoniae with iscom matrix containing 5 μg QA/mouse dose |
| E | 10 μg M. hyopneumoniae with iscom matrix containing 2.5 μg QA/mouse dose |
| F | 10 μg M. hyopneumoniae with iscom matrix containing 1.25 μg QA/mouse dose |
| G | 0 μg M. hyopneumoniae with iscom matrix containing 5 μQA/mouse dose |
| H | 10 μg M. hyopneumoniae + $10^7$ cfu H. pleuropneumoniae with iscom matrix containing 5 μg QA/mouse dose |

QA = Quil A

Groups of mice were pre-bled via the tail vein prior to primary immunisation and then fourteen days later. Twenty-eight days after the primary immunisation the animals received a further vaccination and were bled 7 days later and finally 28 days post secondary. Serum was separated from the blood on the day of collection and stored at −70° C. for analysis by ELISA. Mice were observed following vaccination for any adverse local and systemic reactions.

Results

The results of the experiments designed to assess the adjuvant effect of Quil A in an iscom preparation where the antigen is external to the preparation are shown below in Tables 1 and 2.

The results clearly demonstrate that the ISCOM preparation with the highest protein: Quil A ratio of 10 μg: 10 μg/mouse dose produces the greatest response to the vaccine, giving a response as good as if not better than the Freund's adjuvanted vaccine.

Groups of mice receiving iscom vaccines containing less than 10 μg of Quil A per mouse dose performed no better, in producing a response to the antigen, than the unadjuvanted antigen alone.

No vaccine reactions either local or systemic were noted in any mice receiving iscom vaccine or with antigen alone. In mice immunised with Freund's, small granulomas approximately 3 mm were noted at the immunisation point but as with all the other mice no signs of systemic disturbances were noted.

TABLE 1

Anti M. hyopneumoniae response in mice as measured by the INDIRECT ELISA

| Groups/ Time | Pre Vaccination | 28DP2° |
|---|---|---|
| A | 0.023 | 0.184 |
| B | 0.019 | 0.126 |
| C | 0.019 | 0.203 |
| D | 0.019 | 0.043 |
| E | 0.019 | 0.083 |
| F | 0.032 | 0.029 |
| G | 0.042 | 0.052 |
| H | 0.040 | 0.150 |

Standard Deviations omitted
DP2° - days post secondary vaccination

EXAMPLE 8:

Mouse Studies: Evaluation of Empty iscom matrix as an adjuvant for Haemophilus pleuropneumoniae vaccine in mice Mice were immunised with vaccines containing whole inactivated H. pleuropneumoniae bacteria and iscom matrix formulated with varying levels of Quil A. Mice immunised twice with a vaccine containing 10 μg Quil A/mouse gave a greater antibody response than mice immunised with equivalent numbers of bacteria in Freund's adjuvant. Lower doses of Quil A had little apparent adjuvant effect. No adverse local or systemic effects were observed following administration of any vaccine containing iscom matrix.

The NCTC reference strain of H. pleuropneumoniae serotype 3 (Strain 1421) was grown to log phase growth in Yeast extract medium supplemented with B AND. The culture was inactivated with 0.2% formalin and washed three times with phosphate buffered saline (PBS) to yield a washed, inactivated whole cell antigen preparation. The antigen was standardised by enumeration of bacteria using a Neubaumer chamber with modified Thoma rulings and was stored in PBS at 4° C. until use.

Groups of mice, six per group, were immunised with H. pleuropneumoniae alone, H. pleuropneumoniae in FIA, or H. pleuropneumoniae together with iscom matrix containing different levels of Quil A, as detailed below. A final group received both H. pleuropheumoniae and M. hyopneumoniae antigens together with iscom matrix to investigate possible interaction between the two antigens. Mice received two subcutaneous injections of 0.1 ml of the appropriate vaccine on two occasions with a 3 week interval between imunisations.

| | Immunisation of mice |
|---|---|
| Group | Vaccination |
| 1 | None |
| 2 | Hpl alone |
| 3 | Hpl in FIA |
| 4 | Hpl with iscom matrix containing 10 μg QA/per mouse dose of vaccine |
| 5 | Hpl with iscom matrix containing 5 μg QA/per mouse dose of vaccine |
| 6 | Hpl with iscom matrix containing 2.5 μg QA/per mouse dose of vaccine |
| 7 | Hpl with iscom matrix containing 1.2 μg QA/per mouse dose of vaccine |
| 8 | Hpl with iscom matrix containing 5 μg QA/per mouse dose of vaccine and 10 μg/per mouse dose Mycoplasma hyopneumoniae antigen. |

Following primary vaccination there was little antibody response in any group. Following secondary vaccination there was a rapid and pronounced rise in antibody levels in 2 out of the 8 groups immunised. The greatest response was seen in mice immunised with bacteria together with iscom matrix containing 10 μg/mouse Quil A which had a mean peak OD of 1.24 (±0.17) Units of Optical Density (UOD) when measured one week after secondary immunisation. Mice immunised with bacteria and FIA had a similar but slightly smaller antibody response with a mean peak OD of 1.11 (0.08) UOD on the same occasion. Mice immunised with bacteria alone, bacteria with lower doses of Quil A, or bacteria together with M. hyop-

*neumoniae* antigen all had similar, lower, antibody responses with peak values of between 0.43 and 0.63 UOD when measured one month after secondary immunisation.

TABLE 2

Anti - *H. pleuropneumoniae* response, as measured by indirect ELISA

| | Pre-vaccination | 28 DP2 |
|---|---|---|
| A | 0.87 | 0.189 |
| B | 0.170 | 0.428 |
| C | 0.185 | 1.002 |
| D | 0.135 | 1.161 |
| E | 0.131 | 0.626 |
| F | 0.164 | 0.645 |
| G | 0.119 | 0.620 |
| H | 0.227 | 0.480 |

We claim:

1. A process for making an immunogenic complex comprising a water-insoluble antigen, the process comprising solubilising the antigen with a solubilising agent, admixing the solubilised antigen, a glycoside and a sterol and forming iscoms without removal of the solubilising agent.

2. A process according to claim 1 wherein the solubilising agent is sodium desoxycholate, octylglucoside, nonyl N-methyl glucamide, decanoyl N-methyl glucamide or a polyethylene glycol p-isooctyl-phenylether having 9 to 10 oxyethylene groups.

3. A process according to claim 1 wherein a phospholipid is admixed with the solubilzed antigen, glycoside and sterol.

4. A process according to claim 3 wherein the phospholipid is phosphatidylcholine.

5. A process according to claim 1 wherein the glycoside is Quil A.

6. A process according to claim 1 wherein the sterol is cholesterol.

* * * * *